US00PP35751P2

(12) United States Plant Patent
Mathey

(10) Patent No.: US PP35,751 P2
(45) Date of Patent: Apr. 16, 2024

(54) ***TECOMA* PLANT NAMED 'SMNTSC'**

(50) Latin Name: *Tecoma stans*
Varietal Denomination: SMNTSC

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,934

(22) Filed: Aug. 30, 2023

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Tecoma* plant named 'SMNTSC', characterized by its relatively compact, upright to somewhat outwardly spreading and mounding plant habit; moderately vigorous growth habit and moderate growth rate; freely branching habit; medium green-colored leaves; freely flowering habit; large inflorescences with large bright yellow-colored flowers; and good garden performance.

2 Drawing Sheets

Figure 1:
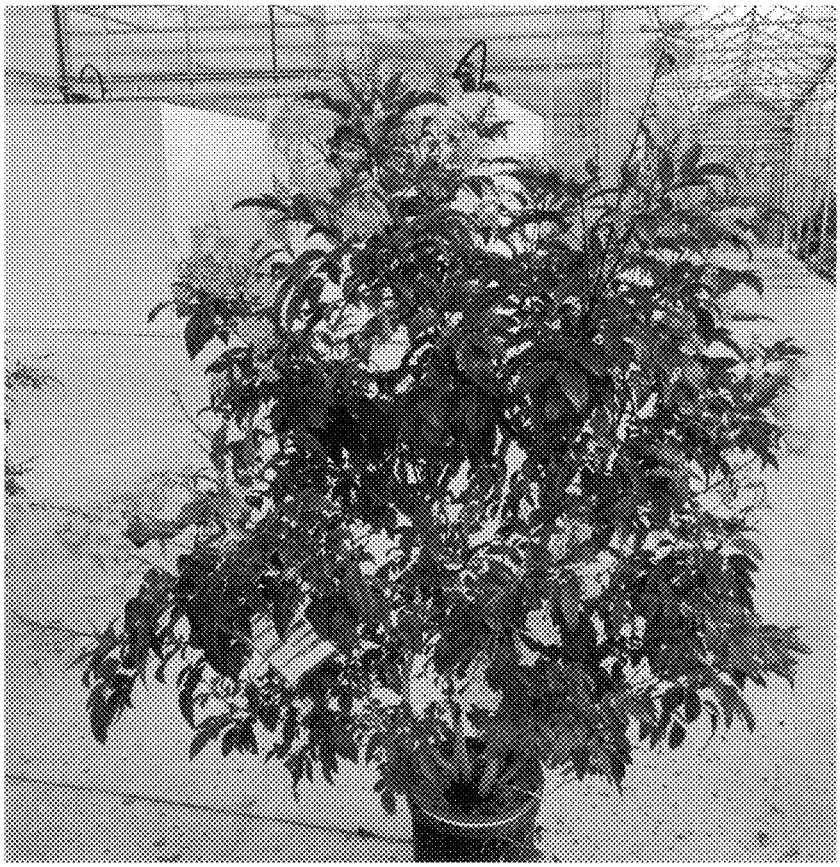

Botanical designation: *Tecoma stans.*
Cultivar denomination: 'SMNTSC'.

BACKGROUND OF THE INVENTION

The present invention relates to a new and distinct cultivar of *Tecoma* plant, commonly referred to as Trumpetbush, botanically known as *Tecoma stans* and hereinafter referred to by the name 'SMNTSC'.

The new *Tecoma* plant is a product of a planned breeding program conducted by the Inventor in Grand Haven, Michigan. The objective of the breeding program is to create new freely-flowering *Tecoma* plants with attractive and vibrant flowers.

The new *Tecoma* plant originated from an open-pollination in 2019 of *Tecoma stans* 'Yellow Bells', not patented, as the female, or seed, parent with an unknown selection of *Tecoma stans*, as the male, or pollen, parent. The new *Tecoma* plant was discovered and selected by the Inventor in 2020 as a single flowering plant within the progeny of the stated open-pollination in a controlled environment in Grand Haven, Michigan.

Asexual reproduction of the new *Tecoma* plant by softwood cuttings in a controlled greenhouse environment in Grand Haven, Michigan since 2020 has shown that the unique features of this new *Tecoma* plant are stable and reproduced true to type in successive generations of asexual reproduction.

SUMMARY OF THE INVENTION

Plants of the new *Tecoma* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNTSC'. These characteristics in combination distinguish 'SMNTSC' as a new and distinct *Tecoma* plant:

1. Relatively compact, upright to somewhat outwardly spreading and mounding plant habit.
2. Moderately vigorous growth habit and moderate growth rate.
3. Freely branching habit.
4. Medium green-colored leaves.
5. Freely flowering habit.
6. Large inflorescences with large bright yellow-colored flowers.
7. Good garden performance.

Plants of the new *Tecoma* can be compared to plants of the female parent, 'Yellow Bells'. Plants of the new *Tecoma* differ primarily from plants of 'Yellow Bells' in flower color as plants of the new *Tecoma* are brighter yellow in color than plants of 'Yellow Bells'. In addition, plants of the new *Tecoma* have larger flowers than plants of 'Yellow Bells'.

Plants of the new *Tecoma* can be compared to plants of the *Tecoma stans* 'Mayan Gold', not patented. In side-by-side comparisons, plants of the new *Tecoma* differ primarily from plants of 'Mayan Gold' in the following characteristics:

1. Plants of the new *Tecoma* have longer inflorescences with more flowers per inflorescence than plants of 'Mayan Gold'.
2. Flowers of plants of the new *Tecoma* are much larger than flowers of plants of 'Mayan Gold'.

BRIEF DESCRIPTION OF THE PHOTOGRAPHS

The accompanying colored photographs illustrate the overall appearance of the new *Tecoma* plant showing the colors as true as it is reasonably possible to obtain in colored reproductions of this type. Colors in the photographs may differ slightly from the color values cited in the detailed botanical description which accurately describe the colors of the new *Tecoma* plant.

The photograph on the first sheet (FIG. 1) is a side perspective view of typical flowering plants of 'SMNTSC' grown in a container.

Figure 2:
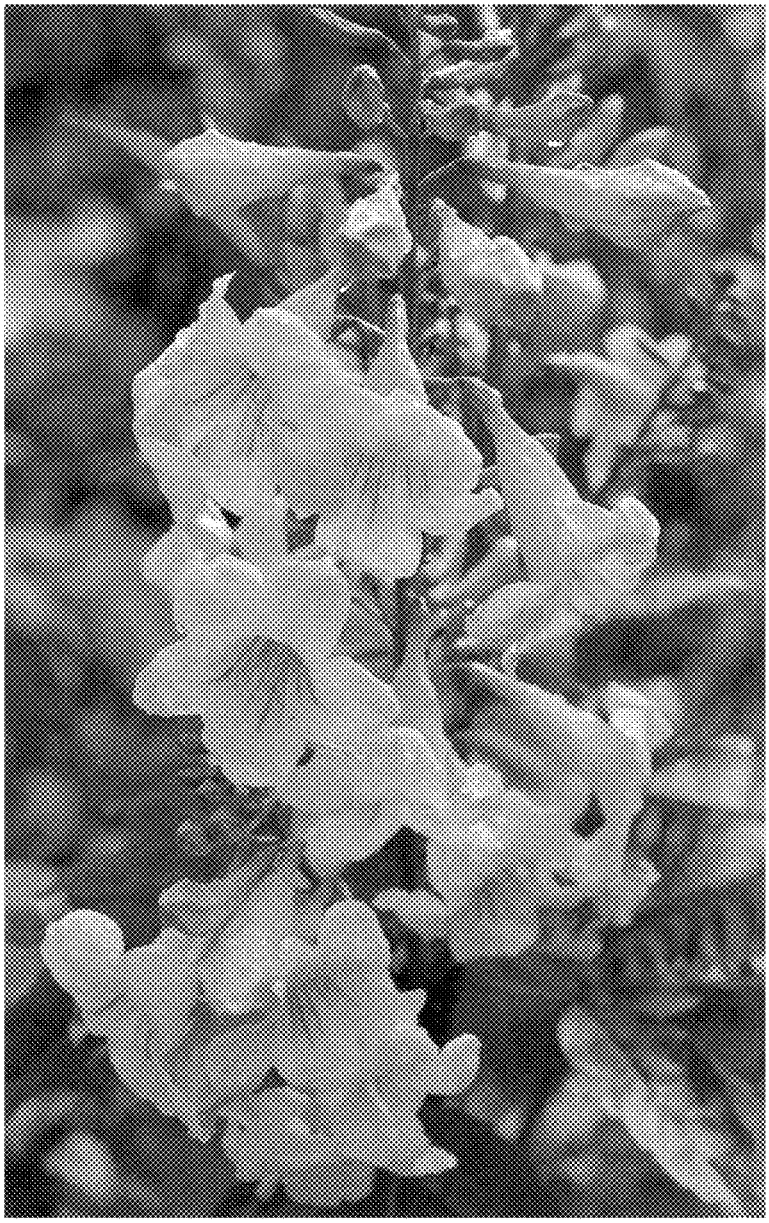

The photograph on the second sheet (FIG. 2) is a close-up view of a typical inflorescence of 'SMNTSC'.

DETAILED BOTANICAL DESCRIPTION

Plants used for the following description were grown during the early summer in two-gallon containers in a polyethylene-covered greenhouse and in an outdoor nursery in Grand Haven, Michigan and under cultural practices typical of commercial *Tecoma* production. During the production of the plants, day temperatures ranged from 18° C. to 27° C. and night temperatures ranged from 5° C. to 10° C. Plants of the new *Tecoma* were three years old when the photographs were taken and two years old when the description was taken. In the following description, color references are made to The Royal Horticultural Society Colour Chart, 2015 Edition, except where general terms of ordinary dictionary significance are used.

Botanical classification: *Tecoma stans* 'SMNTSC'.

Parentage:

- *Female, or seed, parent.*—*Tecoma stans* 'Yellow Bells', not patented.
- *Male, or pollen, parent.*—Unknown selection of *Tecoma stans*.

Propagation:

- *Type.*—By softwood cuttings.
- *Time to initiate roots, summer.*—About 35 days at temperatures about 18° C. to 27° C.
- *Time to produce a rooted young plant, summer.*—About eight weeks at temperatures about 18° C. to 27° C.
- *Root description.*—Fine to thick; fibrous; typically white in color, actual color of the roots is dependent on substrate composition, water quality, fertilizer, substrate temperature and physiological age of roots.
- *Rooting habit.*—Freely branching; medium density.

Plant description:

- *Plant form and growth habit.*—Perennial shrub; relatively compact, upright to outwardly spreading and mounding plant habit; moderately vigorous growth habit and moderate growth rate.
- *Branching habit.*—Freely branching habit, about 10 to 15 primary lateral branches develop per plant.
- *Plant height.*—About 55 cm.
- *Plant diameter* (*area of spread*).—About 45 cm.

Lateral branch description:

- *Length.*—About 45 cm.
- *Diameter.*—About 3 mm.
- *Internode length.*—About 3 cm.
- *Aspect.*—About 45 to 75 degrees from vertical.
- *Strength.*—Strong.
- *Texture.*—Smooth, glabrous.
- *Color, developing.*—Closest to 144A.
- *Color, developed.*—Closest to 200A with lenticels, closest to 199C.

Leaf & leaflet description:

- *Arrangement.*—Opposite, compound; leaves with seven leaflets.
- *Leaf length.*—About 14 cm.
- *Leaf width.*—About 10 cm.
- *Leaflet length.*—About 7 cm.
- *Leaflet width.*—About 3 cm.
- *Leaflet shape.*—Narrowly elliptic.
- *Leaflet apex.*—Acute.
- *Leaflet base.*—Cuneate.
- *Leaflet margin.*—Serrate.
- *Leaflet texture, upper surface.*—Smooth, glabrous.
- *Leaflet texture, lower surface.*—Smooth, glabrous; venation, pronounced.
- *Leaflet venation pattern.*—Pinnate.
- *Leaflet color.*—Developing and fully expanded leaves, upper surface: Closest to 137B; venation, closest to 144C. Developing and fully expanded leaves, lower surface: Closest to 146B; venation, closest to 144C.
- *Petioles and petiolules.*—Petiole length: About 9 cm. Petiole diameter: About 2 mm. Petiolule length: About 1 mm. Petiolule diameter: About 1 mm. Petiole and petiolules texture, upper and lower surfaces: Smooth, glabrous. Petiole and petiolules color, upper and lower surfaces: Closest to 144C.

Flower description:

- *Flower arrangement and flowering habit.*—Single salverform flowers arranged in terminal racemes; freely flowering habit with usually about 20 flowers developing per inflorescence; flowers face mostly outwardly.
- *Natural flowering season.*—Plants of the new *Tecoma* flower throughout the summer in Michigan; flowers not persistent.
- *Fragrance.*—Mildly fragrant; pleasant and sweet.
- *Inflorescence height.*—About 12 cm.
- *Inflorescence diameter.*—About 8 cm.
- *Flower diameter.*—About 3 cm.
- *Flower depth.*—About 3 cm.
- *Flower throat diameter.*—About 1 cm.
- *Flower tube length.*—About 2.5 cm.
- *Flower tube diameter, proximally.*—About 3 mm.
- *Flower buds.*—Length: About 1.5 cm. Diameter: About 3 mm. Shape: Obovate. Color: Closest to N144D.
- *Petals.*—Quantity and arrangement: Single whorl of five petals; fused with apices free. Lobe length: About 1 cm. Lobe width: About 1.25 cm. Lobe shape: Orbicular. Apex: Obtuse; occasionally, retuse. Margin: Entire to slightly crenate. Texture, upper and lower surfaces: Smooth, glabrous; soft. Texture, throat and tube: Smooth, glabrous; soft. Color: When opening and fully opened, upper surface: Closest to 9B with occasional sectors of closest to 13B; venation, similar to lamina colors; color does not change with subsequent development. When opening and fully opened, lower surface: Closest to 9B; venation, closest to 9B; color does not change with subsequent development. Throat: Closest to 9B; venation, closest to 165B. Tube: Closest to 9B; venation, closest to 9B.
- *Sepals.*—Quantity and arrangement: Single whorl of five small sepals; fused towards the base forming a campanulate-shaped calyx. Length: About 2 mm. Width: About 1 mm. Shape: Narrowly deltoid. Apex: Acute. Margin: Entire. Texture, upper and lower surfaces: Smooth, glabrous. Color, upper and lower surfaces: Closest to 144B.

*Peduncles.*—Length: About 10 cm. Diameter: About 2 mm. Strength: Strong. Aspect: About 90 degrees from the stem axis. Texture: Smooth, glabrous. Color: Closest to 144B.

*Pedicels.*—Length: About 8 mm. Diameter: About 1 mm. Strength: Strong. Aspect: About 45 degrees from peduncle axis. Texture: Smooth, glabrous. Color: Closest to 144B.

*Reproductive organs.*—Androecium: Quantity of stamens per flower: Four. Filament length: About 1 cm. Filament color: Close to N144B. Anther length: About 3 mm. Anther shape: Linear. Anther color: Closest to 8D. Amount of pollen: Moderate. Pollen color: Closest to 8D. Gynoecium: Quantity of pistils per flower: One. Pistil length: About 2 cm. Stigma shape: Roughly ovoid. Stigma color: Closest to N144B. Style length: About 2 mm. Style color: Closest to N144B. Ovary color: Closest to N144B.

*Seeds and fruits.*—To date, seed and fruit development have not been observed on plants of the new *Tecoma*.

Garden performance: Plants of the new *Tecoma* have been observed to have good garden performance and to tolerate rain, wind and temperatures ranging from about −31° C to about 38° C.

Pathogen & pest resistance: To date, plants of the new *Tecoma* have not been observed to be resistant to pathogens and pests common to *Tecoma* plants.

It is claimed:

1. A new and distinct *Tecoma* plant named 'SMNTSC' as illustrated and described.

* * * * *